United States Patent [19]

Bergeron, Jr.

[11] Patent Number: 5,840,739
[45] Date of Patent: Nov. 24, 1998

[54] THIAZOLINE ACID DERIVATIVES

[75] Inventor: Raymond J. Bergeron, Jr., Gainesville, Fla.

[73] Assignee: University of Florida Research Foundation, Inc., Gainesville, Fla.

[21] Appl. No.: 624,289

[22] Filed: Mar. 29, 1996

Related U.S. Application Data

[63] Continuation-in-part of Ser. No. 532,805, Nov. 9, 1995, which is a continuation of Ser. No. 976,635, filed as PCT/US93/10936 Nov. 12, 1993, abandoned.

[51] Int. Cl.⁶ ....................... A61K 31/425; C07D 277/56
[52] U.S. Cl. .......................... 514/365; 514/312; 514/314; 514/342; 546/153; 546/167; 546/280; 548/200; 548/201; 548/204

[58] Field of Search ...................... 548/201, 200, 548/204; 546/280, 153, 167; 514/365, 314, 342, 312

[56] References Cited

U.S. PATENT DOCUMENTS 4,406,905  9/1983  Zähner et al. ........................ 424/263

OTHER PUBLICATIONS

Bergeron, J. Med. Chem. 37 (10), 1411, 1994.

*Primary Examiner*—Robert Gerstl
*Attorney, Agent, or Firm*—Kerkam, Stowell, Kondracki & Clarke; Dennis P. Clarke

[57] ABSTRACT

Thiazoline acids and derivatives useful as chelators of trivalent metals in therapeutic applications have been prepared.

10 Claims, No Drawings

THIAZOLINE ACID DERIVATIVES

This application is a continuation-in-part of application Ser. No. 08/532,805 filed Nov. 9, 1995, which claims priority based on International Patent Application No. PCT/US 93/10936 filed Nov. 12, 1993, which is a continuation of U.S. Ser. No. 07/976,635 filed Nov. 16, 1992, abandoned.

BACKGROUND OF THE INVENTION

Research leading to the completion of the invention was supported in part by Grant Nos. 3203522-12, RO1HL42817 and RO1DK49108 awarded by the National Institutes of Health (NIH). The United States Government has certain rights in and to the claimed invention.

1. Field of the Invention

The present invention relates to novel thiazoline acids and derivatives thereof useful as chelators of trivalent metals in therapeutic applications.

2. Discussion of the Prior Art

While many organisms are auxotrophic for Fe (III), because of the insolubility of the hydroxide ($K_{sp}=1\times10^{-38}$) [*Acc. Chem. Res.*, Vol. 12, Raymond et al, "Coordination Chemistry and Microbial Iron Transport," pages 183–190 (1979)] formed under physiological conditions, nature has developed rather sophisticated iron storage and transport systems. Microorganisms utilize low molecular weight ligands, siderophores, while eukaryotes tend to utilize proteins to transport iron, e.g., transferrin, and store iron, e.g., ferritin [*Trends in Biochem. Sci.*, Vol. 11, Bergeron, "Iron: A Controlling Nutrient in Proliferative Processes," pages 133–136 (1986)].

Iron metabolism in primates is characterized by a highly efficient recycling process with no specific mechanism for eliminating this transition metal [*Clin. Physiol. Biochem.*, Vol. 4, Finch et al, "Iron Metabolism," pages 5–10 (1986); *Ann. Rev. Nutri.*, Vol. 1, Hallberg, "Bioavailability of Dietary Iron in Man," pages 123–147 (1981); *N. Engl. J., Med.*, Vol. 306, Finch et al, "Perspectives in Iron Metabolism," pages 1520–1528 (1982); and *Medicine (Baltimore)*, Vol. 49, Finch et al, "Ferrokinetics in Man," pages 17–53 (1970)]. Because it cannot be effectively cleared, the introduction of "excess iron" into this closed metabolic loop leads to chronic overload and ultimately to peroxidative tissue damage [*The Molecular Basis of Blood Diseases*, Seligman et al, "Molecular Mechanisms of Iron Metabolism," page 219 (1987); *Biochem. J.*, Vol. 229, O'Connell et al, "The Role of Iron in Ferritin- and Haemosiderin-Mediated Lipid Peroxidation in Liposomes," pages 135–139 (1985); and *J. Biol. Chem.*, Vol. 260, Thomas et al, "Ferritin and Superoxide-Dependent Lipid Peroxidation," pages 3275–3280 (1985)]. There are a number of scenarios which can account for "iron overload," e.g., high-iron diet, acute iron ingestion or malabsorption of the metal. In each of these situations, the patient can be treated by phlebotomy [*Med. Clin. N. Am.*, Vol. 50, Weintraub et al, "The Treatment of Hemochromatosis by Phlebotomy," pages 1579–1590 (1966)]. However, there are iron-overload syndromes secondary to chronic transfusion therapy, e.g., aplastic anemia and thalassemia, in which phlebotomy is not an option [*Iron in Biochemistry and Medicine*, Vol. II, Hoffbrand, "Transfusion Siderosis and Chelation Therapy," page 499 (London, 1980)]. The patient cannot be bled, as the origin of the excess iron is the transfused red blood cells; thus, the only alternative is chelation therapy. However, to be therapeutically effective, a chelator must be able to remove a minimum of between 0.25 and 0.40 mg of Fe/kg per day [*Semin. Hematol.*, Vol. 27, Brittenham, "Pyridoxal Isonicotinoyl Hydrazone: An Effective Iron-Chelator After Oral Administration," pages 112–116 (1990)].

Although considerable effort has been invested in the development of new therapeutics for managing thalassemia, the subcutaneous (sc) infusion of desferrioxamine B, a hexa-coordinate hydroxamate iron chelator produced by *Streptomyces pilosus* [*Helv. Chim. Acta*, Vol. 43, Bickel et al, "Metabolic Properties of Actinomycetes. Ferrioxamine B," pages 2129–2138 (1960)], is still the protocol of choice. Although the drug's efficacy and long-term tolerability are well-documented, it suffers from a number of shortcomings associated with low efficiency and marginal oral activity.

Although a substantial number of synthetic iron chelators have been studied in recent years as potential orally active therapeutics, e.g., pyridoxyl isonicotinoyl hydrazone (PIH) [*FEBS Lett.*, Vol. 97, Ponka et al, "Mobilization of Iron from Reticulocytes: Identification of Pyridoxal Isonicotinoyl Hydrazone as a New Iron Chelating Agent," pages 317–321 (1979)], hydroxypyridones [*J. Med. Chem.*, Vol. 36, Uhlir et al, "Specific Sequestering Agents for the Actinides. 21. Synthesis and Initial Biological Testing of Octadentate Mixed Catecholate-hydroxypyridinonate Ligands," pages 504–509 (1993); and *Lancet*, Vol. 1, Kontoghiorghes et al, "1,2-Dimethyl-3-hydroxypyrid-4-one, an Orally Active Chelator for the Treatment of Iron Overload," pages 1294–1295 (1987)] and bis(o-hydroxybenzyl)-ethylenediaminediacetic acid (HBED) analogues [*Ann. N.Y. Acad. Sci.*, Vol. 612, Grady et al, "HBED: A Potential Oral Iron Chelator," pages 361–368 (1990)], none has yet proven to be completely satisfactory. Interestingly, the siderophores have remained relatively untouched in this search. Their evaluation as iron-clearing agents has not at all paralleled the rate of their isolation and structural elucidation. In fact, until recently, beyond DFO, only two of some 100 siderophores identified have been studied in animal models: enterobactin [*Gen. Pharmac.*, Vol. 9, Guterman et al, "Feasibility of Enterochelin as an Iron-Chelating Drug: Studies with Human Serum and a Mouse Model System," pages 123–127 (1978)] and rhodotorulic acid [*J. Pharmacol. Exp. Ther.*, Vol. 209, Grady et al, "Rhodotorulic Acid-Investigation of its Potential as an Iron-Chelating Drug," pages 342–348 (1979)]. While the former was only marginally effective at clearing iron, the latter compound was reasonably active. Unfortunately, both of these cyclic siderophores exhibited unacceptable toxicity, and neither possessed any oral activity. They were abandoned as there were any number of synthetic chelators with equally unsatisfactory properties from which to choose.

U.S. Pat. No. 4,406,905 and Bergeron et al, *J. Med. Chem.*, Vol. 34, No. 7, pages 2072–2078 (1991), the entire contents and disclosures of both of which are incorporated herein by reference, disclose that desferrithiocin and certain 2-pyridyl-2-thiazoline-4-carboxylic acids and derivatives thereof are useful in the treatment of iron overload conditions.

It is an object of the present invention to provide novel thiazoline acids and derivatives thereof which, because of different volumes of distribution in patients and different lipophilicities than the derivatives of the prior art, provide the ability to control the pharmacokinetic properties and toxicities of the drugs.

Another object of the present invention is to provide novel pharmaceutical compositions for and methods of treatment of human and non-human animals in need of therapy entailing the prevention of deposition of trivalent metals and compounds thereof in tissues thereof, as well as the elimination of such metals and compounds from systems overloaded therewith.

SUMMARY OF THE INVENTION

The above and other objects are realized by the present invention, one embodiment of which relates to compounds of the formulae:

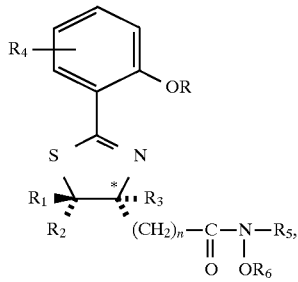
(I)

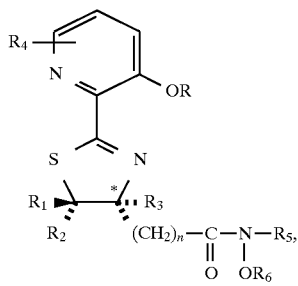
(II)

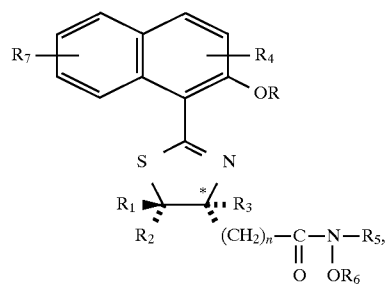
(III)

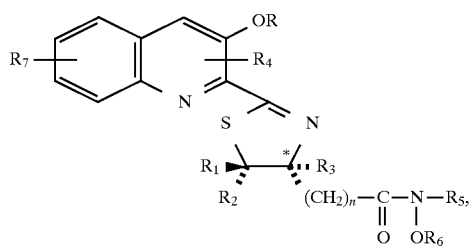
(IV)

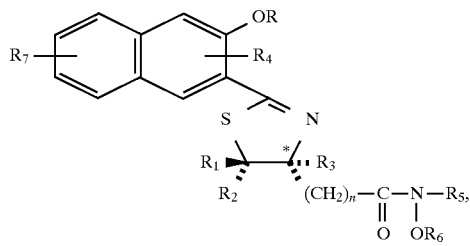
(V)

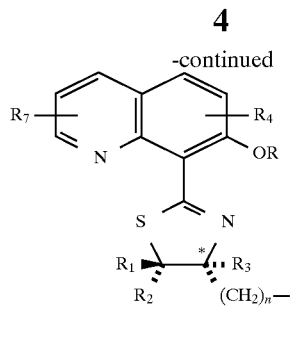
(VI)

wherein: R may be H or acyl, e.g., acetyl, propionyl, butyryl, benzoyl, and the like;

$R_1$, $R_2$, $R_3$, $R_4$ and $R_7$ may be the same or different and represent H, alkyl or hydrocarbyl arylalkyl having up to 14 carbon atoms, or

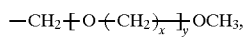

wherein x is 1–10 and y is 0–10;

$R_5$ is H, alkyl or hydrocarbyl aralkyl having up to 15 carbon atoms,

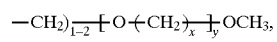

wherein x is 1–10 and y is 0–10, or

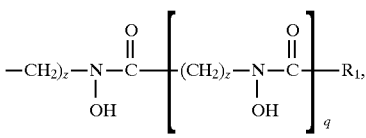

wherein $R_1$ is as defined above, z is 1–10 and q is 0–5;

$R_6$ is H or acyl, as above;

n is 0–10;

a salt thereof with a pharmaceutically acceptable acid, or a pharmaceutically acceptable complex thereof.

A further embodiment of the invention comprises a pharmaceutical composition in unit dosage form comprising a therapeutically effective amount of the above compound and a pharmaceutically acceptable carrier therefor.

An additional embodiment of the invention concerns a method of preventing or treating a pathological condition in a human or non-human animal that is associated with an excess of a trivalent metal, ion or compound thereof comprising administering to the animal a therapeutically effective amount of the above compound.

Another embodiment of the invention relates to compounds of the formulae:

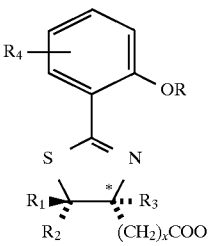
(VII)

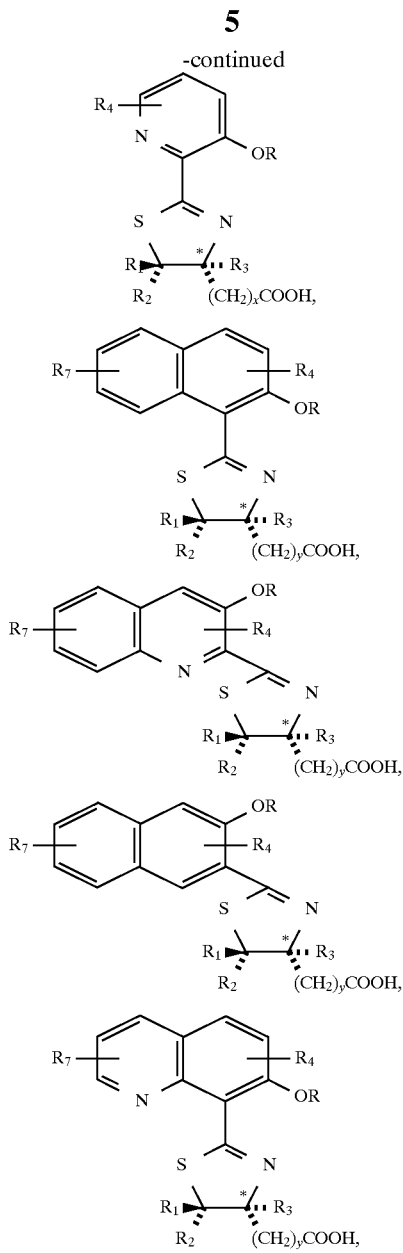

wherein: R may be H or acyl, e.g., acetyl, propionyl, butyryl, benzoyl, and the like;

$R_1$, $R_2$, $R_3$, $R_4$ and $R_7$ may be the same or different and represent H, alkyl or hydrocarbyl arylalkyl having up to 14 carbon atoms, or

x is 1–10; and
y is 0–10;

or a pharmaceutically acceptable salt or complex thereof.

DETAILED DESCRIPTION OF THE INVENTION

The present invention is predicated on the discovery that compounds of the above formulae I–XII are valuable bioactive chelators or sequestrants for trivalent metals such as Fe, Al and Cr. They can be administered to human and non-human mammals to prevent the deposition of, e.g., iron, in the tissues thereof. They are also useful for the elimination of, e.g., iron, from such mammals afflicted with, e.g., haemochromatosis, haemosiderosis and also cirrhosis. They also find application in dialysis, encephalopathy, osteomalacia and Alzheimer's disease.

The compounds of formulae I–XII are characterized by the asymmetric carbon atom marked with an asterisk (*). The bonds surrounding these carbon atoms are arranged tetrahedrally and the substituents thus bonded to the asymmetric carbon atoms are in fixed positions. The compounds of formulae I–XII represent optical antipodes exhibiting either the (S) or (R) conformation as shown in (i) and (ii) below:

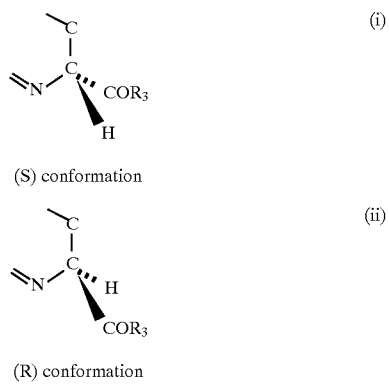

In the above formulae I–XII, R is preferably H, but may also be a suitable acyl group which is cleavable under physiological conditions to the free hydroxyl compounds and a biologically acceptable acid. Such acyl groups are known in the art, e.g., the acyl radical of a carbonic acid semiester, in particular carbonic acid semi-$C_1$–$C_4$-alkyl ester or carbonic acid semi-oxaalkyl ester in which oxaalkyl has 4–13 chain members such as an acyl radical —C(=O)—(O—CH$_2$—CH$_2$)$_n$—O—Alk in which n is an integer from 0 to 4 and Alk represents $C_1$–$C_4$ alkyl, in particular methyl or ethyl. Such acyl groups are, for example, methoxycarbonyl, ethoxycarbonyl or 2-(methoxyethoxy)-ethoxycarbonyl. Further acyl radicals are, for example, $C_1$–$C_3$-alkanoyl such as acetyl or propionyl, or mono-substituted or di-substituted carbamoyl such as di-$C_1$–$C_4$-alkyl carbamoyl, for example, dimethylcarbamoyl or diethylcarbamoyl, or $C_1$–$C_4$-alkoxycarbonyl-$C_1$–$C_4$-alkylcarbamoyl, for example, methoxycarbonylmethylcarbamoyl, ethoxycarbonylmethylcarbamoyl or 2-ethoxycarbonylethylcarbamoyl.

$R_1$, $R_2$, $R_3$, $R_4$ and $R_7$ may be H, straight or branched chain alkyl having up to 14 carbon atoms, e.g., methyl, ethyl, propyl and butyl; arylalkyl wherein the aryl portion is hydrocarbyl and the alkyl portion is straight or branched chain, the arylalkyl group having up to 14 carbon atoms, or

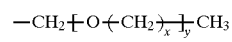

wherein x is 1–10 and y is 0–10.

$R_5$ is preferably straight or branched chain alkyl having up to 15 carbon atoms, but may also be H; —(CH$_2$)$_{1-2}$—[O—(CH$_2$)$_x$—]$_y$OCH$_3$, wherein x is 1–10 and y is 0–10; or

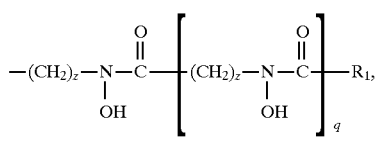

wherein $R_1$ is as defined above, z is 1–10 and q is 0–5.

$R_6$ is preferably H, but may also be acyl as described above.

Exemplary of the compounds of formulae I–XII are (S)-desmethyldesferrithiocin, N-methylhydroxamate; (S)-desmethyldesferrithiocin, N-[5-(acetylhydroxyamino)-pentyl]hydroxamate; 2-(2'-hydroxynaphth-1'-yl) -$\Delta^2$-thiazoline-(4R)-carboxylic acid; 2-(2'-hydroxynaphth-1'-yl) -$\Delta^2$-thiazoline-(4S)-carboxylic acid; 2-(3'-hydroxynaphth-2'-yl)-$\Delta^2$-thiazoline-(4R)-carboxylic acid; and 2-(3'-hydroxynaphth- 2'-yl)-$\Delta^2$-thiazoline-(4S)-carboxylic acid.

It will be understood that salts of the compounds of formulae I–VI with pharmaceutically acceptable acids also comprise part of the present invention. Suitable such acids include hydrochloric, sulfuric or phosphoric acids, as well as methanesulfonic, arginine, lysine, and the like.

The invention also includes pharmaceutically acceptable salts of the carboxylic acids of formulae VII–XII. Thus, ammonium salts and metal salts such as the alkali metal and alkaline earth metals salts, e.g., sodium, potassium, magnesium or calcium salts, as well as divalent metal salts such as zinc, and salts with suitable organic amines, there coming into consideration such salt formation especially aliphatic, cycloaliphatic, cycloaliphatic-aliphatic or araliphatic primary, secondary or tertiary mono-, di- or poly-amines, and also heterocyclic bases. Such amines are, for example, lower alkylamines, for example, triethylamine, hydroxy-lower alkyl-amines, for example, 2-hydroxyethylamine, bis-(2-hydroxyethyl)-amine or tris-(2-hydroxyethyl)-amine, basic aliphatic esters of carboxylic acids, for example, 4-aminobenzoic acid 2-diethylaminoethyl ester, lower alkyleneamines, for example, 1-ethylpiperidine, cycloalkylamines, for example, dicyclohexylamine, or benzylamines, for example, N,N'-dibenzylethylenediamine, also bases of the pyridine type, for example, pyridine, collidine or quinoline. Further salts include internal salts (zwitterionic forms of compounds of the invention), wherein a basic group, for example, the basic nitrogen atom present in the pyridine ring, is protonated by a hydrogen ion originating from an acid group in the molecule.

Owing to their high solubility and good tolerability, metal ion complexes of compounds of the above formulae, especially with suitable paramagnetic and/or radioactive metals, can be used as contrast agents in diagnostic medicine, for example, X-ray, radionuclide, ultrasound and/or magnetic resonance diagnostics.

Compounds of formulae I and II may be synthesized by reacting:

a. a picolinic acid derivative of the formula

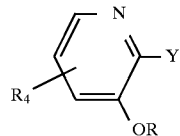

in which R and $R_4$ are as defined above and Y represents carboxy or a reactive functional derivative of a carboxy group, with b. a reactive cysteine derivative of the formula

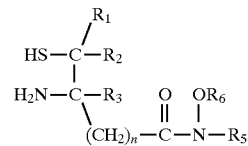

wherein hydroxy groups are optionally protected to produce a compound of formula I or II after splitting off optionally present protective groups and, optionally, conversion to a suitable salt.

Free hydroxy groups present in the compounds of the above formulae are optionally protected by conventional protecting groups. Such protecting groups protect the hydroxy groups from undesired condensation reactions, substitution reactions and the like. The protecting groups can be introduced and removed easily, i.e., without undesirable secondary reactions taking place, for example, by solvolysis or reduction, in a manner known per se. Protecting groups and the methods by which they are introduced and split off are described, for example, in "Protective Groups in organic Chemistry," Plenum Press, London, N.Y. (1973) and also in "Methoden der organischen Chemie," Houben-Weyl, 4th edition, Vol. 15/1, Georg Thieme Verlag, Stuttgart (1974).

Suitable hydroxy-protecting groups are, for example, acyl radicals such as lower alkanoyl optionally substituted, for example, by halogen such as 2,2-dichloroacetyl, or acyl radicals of carbonic acid semiesters, especially tert.-butoxy-carbonyl, optionally substituted benzyloxycarbonyl, for example, 4-nitrobenzyloxycarbonyl, ordiphenylmethoxycarbonyl, alkenyloxycarbonyl, for example, allyloxycarbonyl, or 2-halo-lower alkoxycarbonyl such as 2,2,2-trichloroethoxycarbonyl, also trityl or formyl, or organic silyl radicals, also etherifying groups that can readily be split off such as tert.-lower alkyl, for example, tert.-butyl, or 2-oxa- or 2-thia-cycloalkyl having 5 or 6 ring atoms, for example, tetrahydrofuryl or 2-tetrahydropyranyl or corresponding thia analogues, and also optionally substituted 1-phenyl-lower alkyl such as optionally substituted benzyl or diphenylmethyl, there coming into consideration as substituents of the phenyl radicals, for example, halogen such as chlorine, lower alkoxy such as methoxy, and/or nitro.

A reactive functional derivative of a carboxy group (Y) is, for example, an acid anhydride, an activated ester or an activated amide, cyano, a group of the formula —C(OR$_a$)$_3$ or —C(=NH)—R$_a$ in which R$_a$ is lower alkyl. Corresponding derivatives are well known in the art.

Of the anhydrides, the mixed anhydrides are especially suitable. Mixed anhydrides are, for example, those with inorganic acids such as hydrohalic acids, i.e., the corresponding acid halides, for example, chlorides or bromides, also with hydrazoic acid, i.e., the corresponding acid azides. Further mixed anhydrides are, for example, those with organic carboxylic acids such as with lower alkanecarboxylic acids optionally substituted, for example, by halogen such as fluorine or chlorine, for example, pivalic acid or trichloroacetic acid, or with semiesters, especially lower alkyl semi-esters of carbonic acid such as the ethyl or isobutyl semi-ester of carbonic acid, or with organic, especially aliphatic or aromatic, sulfonic acids, for example, p-toluenesulfonic acid. Of the activated esters, there may be mentioned, for example, esters with vinylogous alcohols (i.e., enols such as vinylogous lower alkenols), or iminomethyl ester halides such as dimethyliminomethyl ester chloride (prepared from the carboxylic acid and, for example, dimethyl-(1-chloroethylidine)iminium chloride of the formula $(CH_3)_2N^{\oplus}=C(Cl)CH_3Cl^{\ominus}$, which can be obtained, for example, from N,N-dimethylacetamide and phosgene), or aryl esters such as preferably suitable substituted phenyl esters, for example, phenyl ester substituted by halogen such as chlorine, and/or by nitro, for example, 4-nitrophenyl ester, 2,3-dinitrophenyl ester or 2,3,4,5,6-pentachlorophenyl ester, N-hetero-aromatic esters such as N-benztriazole esters, for example, 1-benztriazole ester, or N-diacylimino esters such as N-succinylamino or N-phthalylimino ester. Suitable activated amides are, for example, imidazolides, also 1,2,4-triazolides, tetrazolides or 1,2,4-oxadiazolinonides.

The activation of the carboxy group Y in the compounds of the above formulae can also be effected in situ.

A reactive functional derivative of a cysteine of the above formulae is a compound in which the amino and/or mercapto group is activated for the reaction with the carboxy group of a compound of the above formulae, that is to say, is present in nucleophilic form. The amino group is activated, for example, by reaction with a phosphite.

The reaction of the above compounds in which Y represents carboxy with the cysteine derivative is preferably carried out in the presence of a suitable condensation agent or under dehydrating conditions, for example, while removing the water of reaction by azeotropic distillation. Customary condensation agents are, for example, carbodiimides, for example, N,N'-diethyl-, N,N'-dipropyl-, N,N'-dicyclohexyl- or N-ethyl-N'-(3-dimethylaminopropyl)-carbodiimide, suitable carbonyl compounds, for example, carbonyldiimidazole, or 1,2-oxazolium compounds, for example, 2-ethyl-5-phenyl-1,2-oxazolium-3'-sulfonate or 2-tert.-butyl-5-methyl-isoxazolium perchlorate, for a suitable acylamino compound, for example, 2-ethoxy-1-ethoxycarbonyl-1,2-dihydroquinoline, furthermore diphenylphosphoryl azide. The condensation reaction is carried out preferably in an anhydrous reaction medium, preferably in the. presence of a solvent or diluent, for example, methylene chloride, benzene or tetrahydrofuran and, if necessary, while cooling or heating, for example, at ambient temperature or at slightly elevated temperature, and/or in an insert gas atmosphere. If a compound in which Y represents an acid anhydride derivative of a carboxy group is carried out, the reaction is performed under essentially the same conditions in the presence of a basic agent such as the sodium or potassium salt or carbonic acid, or a tertiary amino compound such as a tri-$C_1$-$C_4$-alkyl amine, for example, triethylamine, or a pyridine base such as pyridine or quinoline.

A preferred form of this process according to the invention is the reaction of a compound of the above formulae in which Y represents cyano with a cysteine derivative of the above formulae. The reaction is carried out in an inert solvent such as an aqueous solvent at ambient temperature or, preferably, at slightly elevated temperature, for example, at about 50° to 80° C., and preferably under an inert gas atmosphere.

It is also possible to carry out the above-described process wherein the cysteine derivative is of the formula:

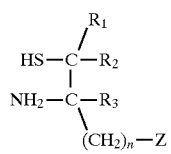

wherein $R_1$, $R_2$ and $R_3$ are as described above and Z is carboxy or a reactive functional derivative thereof, for example, an activated ester to produce a compound of the formula:

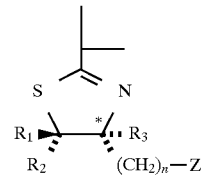

wherein

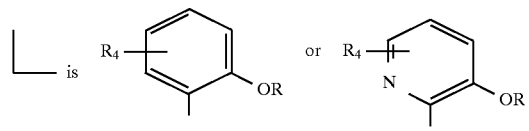

followed by reaction with a compound of the formula

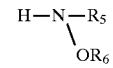

or with a compound which is convertible thereto. A preferred functional derivative of a carboxy group according to the invention is the N-succinylimino ester. The reaction is performed in an inert solvent such as an aprotic solvent, for example, dimethylformamide, dimethylsulfoxide or dioxane or a $C_1$–$C_4$ alkanol such as methanol, at ambient temperature or while cooling, for example, at about 0° C.

In resulting compounds in which one or more functional (hydroxy) groups are protected, the latter can be freed, optionally in stages or simultaneously, in a manner known per se, by means of solvolysis, especially hydrolysis or acidolysis, or in some cases also by means of careful reduction. Silyl protecting groups are advantageously split off with fluorides, for example, tetraethylammonium fluoride.

Compounds of formulae III–XII are prepared by methods differing from those described above since cysteine reacts poorly with 2-hydroxy-1-naphthonitrile. The syntheses of the naphthyl derivatives is dependent on accessing the intermediate imidate. Thus, e.g., ethyl-2-hydroxy-1-naphthimidate is assembled in six steps starting from 2-hydroxy-1-naphthaldehyde. The hydroxyl of aldehyde is alkylated (benzyl chloride/$K_2CO_3$, EtOH, reflux, 39 hours), providing the benzyl ether. The aldehyde function is oxidized to the acid with $NaClO_2$ and sulfamic acid in aqueous acetone at 0° C. for 50 minutes. Conversion to the acid chloride (oxalyl chloride/toluene/DMF, 25° C., 1 hour) and treatment with concentrated $NH_4OH/CH_2Cl_2$ at room temperature for one day yields the amide. The amide is smoothly converted to the ethyl imidate with Meerwein's salt ($Et_3O^+$ $PF_6^-/CH_2Cl_2$) for one day at room temperature. The benzyl protecting group is removed by hydrogenolysis (Pd—C/ ethanol) to yield the key intermediate. Cyclocondensation thereof with L- or D-cysteine in refluxing methanol for two days generates the iron chelators, as the free acid.

The starting material for the synthesis of the naphthyl DFTs is 3-hydroxy-2-naphthoic acid. The hydroxyl group is acylated with acetic anhydride (concentrated $H_2SO_4$, reflux, 5 minutes). The resulting acid is converted to the corresponding acid chloride (oxalyl chloride/toluene/DMF, 25° C., 1 hour); reaction with concentrated $NH_4OH$ ($CH_2Cl_2$, 25° C., 24 hours) results in the ester-cleaved amide. The free hydroxyl is re-acetylated ($AC_2O$/pyridine, 25° C., 30 minutes). Dehydration of the amide and concomitant cleavage of the acetyl group using $SOCl_2$ at reflux for 2 hours furnishes the key nitrile intermediate. It undergoes cyclization with either L- or D-cysteine (methanolic 0.1M phosphate buffer, pH 5.95, 60° C., 1–2 days) to provide the naphthyl chelators.

Salts of compounds of the invention can be manufactured in a manner known per se. Thus, salts of compounds having acidic groups can be formed, for example, by treating with metal compounds such as alkali metal salts of suitable, organic carboxylic acids, for example, the sodium salt of α-ethylcaproic acid, or with inorganic alkali metal or alkaline earth metal salts, for example, sodium bicarbonate, or: with ammonia or a suitable organic amine, preferably stoichiometric quantities or only a small excess of the salt-forming agent being used. Acid addition salts of compounds of the invention are obtained in a customary manner, for example, by treating with an acid or a suitable anion-exchange reagent. Internal salts of compounds of the invention (zwitterionic forms) can be formed, for example, by neutralizing the compounds or salts such as acid addition salts, to the isoelectric point, for example, with weak bases, or by treating with liquid ion exchangers.

Salts can be converted in a customary manner into the free compounds: metal and ammonium salts can be converted into the free compounds, for example, by treating with suitable acids, and acid addition salts, for example, by treating with a suitable basic agent.

The starting materials are available commercially and/or known or can be manufactured by known processes.

The racemate can be split in a manner known per se, for example, after conversion of the optical antipodes into diastereoisomers, for example, by reaction with optically active acids or bases.

The pharmacologically acceptable compounds of the present invention can be used, for example, for the manufacture of pharmaceutical compositions which contain an effective amount of the active substance together or in admixture with inorganic or organic, solid or liquid, pharmaceutically acceptable carriers.

The pharmaceutical compositions according to the invention are those which are suitable for enteral, such as oral, administration and for parenteral, such as subcutaneous, administration to warm-blooded animals, especially humans, and which contain the pharmacologically active substance on its own or together with a pharmaceutically acceptable carrier. The dosage of the active substance depends on the species of warm-blooded animal and on the age and individual condition, the illness to be treated and also on the mode of administration.

The novel pharmaceutical preparations contain from approximately 10% to approximately 95%, and preferably from approximately 20% to approximately 90%, of the active substance. Pharmaceutical compositions according to the invention can, for example, be in unit dose form, such as dragées, tablets, capsules, suppositories or ampoules, and contain from approximately 0.1 g to approximately 3.0 g, and preferably from approximately 0.3 g to approximately 1.0 g, of the active ingredient.

The pharmaceutical compositions of the present invention are manufactured in a manner known per se, for example, by means of conventional mixing, granulating, confectioning, dissolving or lyophilizing processes. Pharmaceutical compositions for oral use can be obtained by combining the active substance with one or more solid carriers, if desired, granulating a resulting mixture and processing the mixture or granulate, if desired or necessary after the addition of suitable adjuncts, to form tablets or dragée cores. In so doing, they can also be incorporated into plastics carriers which release the active substances or allow them to diffuse in controlled amounts.

Suitable carriers are especially fillers such as guars, for example, lactose, saccharose, mannitol or sorbitol, cellulose preparations and/or calcium phosphates, for example, tricalcium phosphate or calcium hydrogen phosphate, also binders such as starches, for example, corn, wheat, rice or potato starch, gelatine, tragacanth, methylcellulose, hydroxypropylmethylcellulose, sodium carboxymethylcellulose and,/or polyvinylpyrrolidone, and/or, if desired, disintegrators such as the above-mentioned starches, also carboxymethyl starch, cross-linked polyvinylpyrrolidone, agar, alginic acid or a salt thereof such as sodium alginate. Adjuncts are especially flow-regulating and lubricating agents, for example, silica, talc, stearic acid or salts thereof such as magnesium or calcium stearate, and/or polyethylene glycol. Dragée cores are provided with suitable coatings that are, if desired, resistant to gastric juice, there being used, inter alia, concentrated sugar solutions which optionally contain gum arabic, talc, polyvinylpyrrolidone, polyethylene glycol and/or titanium dioxide, lacquer solutions in suitable organic solvents or solvent mixtures or, for the manufacture of coatings that are resistant to gastric juice, solutions of suitable cellulose preparations such as acetylcellulose phthalate or hydroxypropylmethylcellulose phthalate. Coloring substances or pigments can be added to the tablets or dragée coatings, for example, for the purpose of identification or for indicating different doses of active substance.

Other orally administrable pharmaceutical compositions are dry-filled capsules made of gelatin and also soft, sealed capsules made of gelatin and a plasticizer such as glycerol or sorbitol. The dry-filled capsules may contain the active ingredient in the form of a granulate, for example, in admixture with fillers such as corn starch, binders and/or glidants such as talc or magnesium stearate and optionally stabilizers. In soft capsules, the active ingredient is preferably dissolved or suspended in suitable liquids or wax-like substances such as fatty oils, paraffin oil or polyethylene glycols, it being possible also for stabilizers to be added.

Other forms of oral administration are, for example, syrups prepared in a customary manner that contain the active ingredient in, for example, suspended form and in a concentration of approximately from 5% to 20%, and preferably approximately 10%, or in a similar concentration that provides a suitable single dose when administered, for example, in measures of 5 or 10 ml. Also suitable are, for example, powdered or liquid concentrates for preparing shakes, for example, in milk. Such concentrates can also be packed in single-dose quantities.

Particularly suitable dosage forms for parenteral administration are sterile aqueous solutions of an active ingredient in water-soluble form, for example, a water-soluble salt, or sterile aqueous injection suspensions which contain substances increasing the viscosity, for example, sodium, carboxymethyl cellulose, sorbitol and/or dextran, and optionally stabilizers. In addition, the active ingredient, with or without adjuvants, can also be in lyophilized form and brought into solution prior to parenteral administration by the addition of suitable solvents.

The invention relates also to compositions for diagnostic purposes that contain a suitable metal complex of a compound of the formula in which $R_1$ has the above meanings, $R_2$ represents hydroxy and $R_3$ represents a group of the formula —$N(R_4,R_5)$ in which $R_4$ represents hydroxy and $R_5$ has the above meanings, preferably in the form of an aqueous solution or in the form of a dry preparation.

The invention relates also to a method of treatment of pathological conditions in a mammal, especially human, which as has been described hereinabove, are associated with an excess of a trivalent metal cation such as aluminum or, especially, iron (III), in the body, which method comprises administering, preferably orally, a prophylactically or therapeutically effective amount of a compound of the formula or of a pharmaceutically acceptable salt thereof. There are used for this purpose especially the above-mentioned pharmaceutical compositions, a daily dose of from approximately 100 mg to approximately 2,000 mg, and preferably from approximately 300 mg to approximately 1,000 mg, of a compound of the present invention being administered to a warm-blooded animal of approximately 70 kg body weight. The dosage can be administered orally in several, for example, three, individual doses. For systemic, e.g., subcutaneous, administration, the more water-soluble salt forms of the compounds of the formula, e.g., the sodium salt, are preferred, for example, orally, or alternatively, subcutaneously.

The following examples serve to illustrate the invention, but should not be construed as a limitation thereof. Temperatures are given in degrees Centigrade.

Preparation of Drugs

Drug solutions were prepared in 60% water, 40% Cremophor RH-40.

EXAMPLE 1

(S)-Desmethyldesferrithiocin, N-Methylhydroxamate (4)

BOP (442.3 mg, 1.0 mmol) was added to a solution of 1 (224.2 mg, 1.0 mmol) and N-methylhydroxylamine hydrochloride (83.52 mg, 1.0 mmol) in DMF (8 ml) at 0° C. A solution of diisopropylethylamine (DIEA, 129.2 mg, 1.0 mmol) in DMF (2 ml) was added dropwise to the above solution at 0° C. The mixture was stirred at 0° C. for 15 minutes and at room temperature overnight. Solvent was removed under high vacuum and the residue was treated with EtOAc (30 ml). The organic phase was washed with 10 ml portions of saturated $NaHCO_3$, saturated NaCl, 10% citric acid and saturated NaCl, and solvent was removed by rotary evaporation. Purification of the residue on a Sephadex LH-20 column, eluting with 3% EtOH/toluene, produced 120 mg (47%) of 4 as a yellow solid: $[\alpha]_D$ −41.3° (c 2.34); NMR ($CDCl_3/d_6DMSO$) δ3.27 (s, 3H), 3.53 (dd, 2H, J=9, 6), 5.70 (t, 1H, J=9), 7.30 (d, 2H, J=3), 8.10 (t, 1H, J=3). Anal. ($C_{10}H_{11}N_2O_3S$) C, H, N.

EXAMPLE 2

(S)-Desmethyldesferrithiocin, N-[5-(Acetylhydroxyamino)-pentyl]hydroxamate (5)

BOP (178.7 mg, 0.404 mmol) was added to a solution of 10 (86.0 mg, 0.404 mmol) and 1 (90.58 mg, 0.404 mmol) in DMF (8 ml) at 0° C. A solution of DIEA (52.2 mg, 0.404 mmol) in DMF (2 ml) was added dropwise to the cold solution. The mixture was stirred at 0° C. for 15 minutes and at room temperature overnight. Solvent was removed under high vacuum, and the residue was treated with EtOAc (40 ml). Product was isolated and purified by the procedure of 4 to furnish 93 mg (60%) of 5 as an oil: $[\alpha]_D$ −16.7° (c 9.85); NMR ($CD_3OD$) δ1.30–1.90 (m, 6H), 2.06 (s, 3H), 3.40–3.80 (m, 6H), 5.93 (t, 1H, J=9), 7.33 (d, 2H, J=3), 8.06 (t, 1H, J=3); HRMS calcd. $C_{16}H_{23}N_4O_5S$ 383.1389 [M+1], $C_{16}H_{22}N_4O_5S$ [M], 382.1311, found 383.1406 [M+1], 382.1344 [M].

EXAMPLE 3

2-(2'-Hydroxynaphth-1'-yl)-$\Delta^2$-thiazoline-(4R)-carboxylic Acid (4)

A mixture of 14 (10.11 g, 47.0 mmol) and L-cysteine. (11.39 g, 94.0 mmol) in methanol (670 ml) was heated under reflux for 46 hours under nitrogen. The mixture was filtered and the filtrate concentrated. The residue was taken up in acetone (100 ml). The precipitated ammonium salt of 4 was filtered off, washed with acetone (100 ml) and then taken up in 0.5N hydrochloric acid (200 ml). The mixture was extracted with ethyl acetate (3×150 ml). The organic layer was dried ($Na_2SO_4$) and concentrated, providing 3.86 g (30%) of 4 as yellow crystals, mp 150°–151° C. IR (KBr): 1720 (C=O), 1615 (C=C), 1460 (C—H) $cm^{-1}$. $^1H$ NMR (DMSO-$d_6$): δ8.13 (d, 1 arom H), 7.92 (d, 1 arom H), 7.85 (d, 1 arom H), 7.50 (m, 1 arom H), 7.36 (m, 1 arom H), 7.23 (d, 1 arom H), 5.45 (dd, 1 CH), 3.82 (dd, ½ $CH_2$, $J_{gem}$=12 Hz, $J_{vic}$=9 Hz), 3.73 (dd, ½ $CH_2$, $J_{vic}$=8 Hz). $^1H$ NMR ($CD_3OD$): δ8.25 (d, 1H, J=9 Hz), 7.78–7.87 (m, 2H), 7.46–7.51 (m, 1H), 7.32–7.36 (m, 1H), 7.15 (d, 1H, J=9 Hz), 5.45 (dd, 1H), 3.77–3.90 (m, 2H). $^{13}C$ NMR ($CD_3OD$): δ173.9 (C=N)*, 173.6 (C=O)*, 157.8 (arom CO), 134.4 (arom CH), 133.4 (arom C), 129.7 (arom CH), 129.6 (arom C), 128.4 (arom CH), 124.6 (arom CH), 124.5 (arom CH), 119.7 (arom CH), 111.9 (arom C), 76.4 (CH), 36.3 ($CH_2$) (*=interchangeable). MS (CI, $NH_3$): m/z (%)=274 [M+1] (75), 187 (100). Anal. ($C_{14}H_{11}NO_3S$) C, H, N, S.

EXAMPLE 4

2-(2'-Hydroxynaphth-1'-yl)-$\Delta^2$-thiazoline-(4S)-carboxylic Acid (5)

Compound 5 was prepared from D-cysteine and 14 using the method of 4. The $^1H$ NMR ($CD_3OD$) of 5 is identical with that of 4. HRMS (FAB, m-nitrobenzyl alcohol): calcd. for $C_{14}H_{11}NO_3S$, 274.0538 [M+1]. Anal. ($C_{14}H_{11}NO_3S$) C, H, N.

EXAMPLE 5

2-(3'-Hydroxynaphth-2'-yl)-$\Delta^2$-thiazoline-(4R)-carboxylic Acid (6)

A mixture of 20 (3.77 g, 22.3 mmol) and L-cysteine, (5.40 g, 44.6 mmol) i methanol (133 ml) and 0.1M phosphate buffer (pH 5.95, 66 ml) was stirred at 60° C. for 5 hours under nitrogen. L-Cysteine (2.70 g, 22.3 mmol) was added and the mixture was stirred at 60° C. for an additional 18 hours. After concentration to about 70 ml, 2% $KHCO_3$ (156 ml) was added and the mixture was extracted with ether (3×100 ml). The aqueous layer was acidified to a pH of 3 with 1N hydrochloric acid (75 ml) and extracted with ethyl acetate (3×150 ml). The organic layer was dried ($Na_2SO_4$) and concentrated to furnish 5.34 g (88%) of 6 as yellow crystals, mp 226°–227° C. IR (KBr): 3040 (O—H), 1710 (C=O), 1635 (C=C), 1230 (C—O) $cm^{-1}$. $^1H$ NMR (DMSO-$d_6$): δ13.28 (s, 1 $CO_2H$), 12.15 (s, 1 OH), 8.20 (s, 1 arom H), 8.02 (d, 1 arom H), 7.78 (d, 1 arom H), 7.54 (dd, 1 arom H), 7.37 (s, 1 arom H), 7.36 (dd, 1 arom H), 5.57 (dd, 1H), 3.80 (dd, ½ $CH_2$, $J_{gem}$=12 Hz, $J_{vic}$=9 Hz), 3.71 (dd, ½ $CH_2$, $J_{vic}$=8 Hz). $^1H$ NMR ($CD_3OD$): δ8.09 (s, 1H), 7.84 (d, 1H, J=8 Hz), 7.69 (d, 1H, J=8 Hz), 7.45–7.50 (m, 1H), 7.27–7.34 (m, 2H), 5.49 (t, 1H, J=9 Hz), 3.74 (d, 2H, J=8 Hz). $^{13}C$ NMR (DMSO-$d_6$): δ172.6 (C=N)*, 171.2 (C=O) *, 154.3 (arom CO), 135.9 (arom C), 132.1 (arom CH), 128.7 (arom CH), 117.9 (arom C), 110.6 (arom CH), 76.7 (CH), 33.5 ($CH_2$) (*=interchangeable). Anal. ($C_{14}H_{11}NO_3S$) C, H, N, S.

EXAMPLE 6

2-(3'-Hydroxynaphth-2'-yl) -Δ²-thiazoline-(4S)-carboxylic Acid (7)

Compound 7 was prepared from D-cysteine and 20 using the method of 6. The $^1$H NMR (CD$_3$OD) of 7 is identical with that of 6. Anal. (C$_{14}$H$_{11}$NO$_3$S) C, H, N.

EXAMPLE 7

2-(Benzyloxy)-1-naphthaldehyde (9)

A mixture of 8 (20.00 g, 116 mmol), K$_2$CO$_3$ (16.03 g, 116 mmol) and benzyl chloride (19.11 g, 151 mmol), 17.4 ml) in ethanol (200 ml) was heated under reflux for 39 hours. Water (200 ml) was added and the mixture was extracted with CH$_2$Cl$_2$ (1×200 ml, 2×100 ml). The organic layer was dried (MgSO$_4$) and concentrated. The residue was crystallized from 10:1 cyclohexane/ethyl acetate (400 ml), giving 22.14 g (73%) of 9 as yellow crystals, mp 123°–124° C. (lit. mp 120°–121° C.).

EXAMPLE 8

2-(Benzyloxy)-1-naphthoic Acid (10)

Sulfamic acid (17.28 g, 178 mmol) was added to a solution of 9 (21.11 g, 80.5 mmol) in acetone (420 ml) and water (210 ml) at 0° C. Over a period of 20 minutes, 80% NaClO$_2$ (10.42 g, 92.2 mmol) was added at 0° C. The solution was stirred at 0° C. for 30 minutes and then concentrated to about 200 ml. After dilution with water (200 ml), the mixture was extracted with CH$_2$Cl$_2$ (1×200 ml, 2×100 ml). The organic layer was dried (MgSO$_4$) and concentrated. Crystallization from cyclohexane/ethyl acetate (1:1) generated 19.12 g (85%) of 10 as pale yellow crystals, mp 127°–128° C. (lit. mp 128°–130° C.).

EXAMPLE 9

2-(Benzyloxy)-1-naphthamide (12)

Oxalyl chloride (25.9 ml, 137 mmol) was added to a mixture of 10 (19.12 g, 68.7 mmol) and DMF (4.34 ml) in dry toluene (325 ml). The solution was stirred at room temperature for 1 hour. The toluene phase was separated from the DMF phase and concentrated. The residue was taken up in toluene (300 ml) and concentrated again, affording 20.21 g (99%) of 11 as yellow crystals, which were dissolved in CH$_2$Cl$_2$ (300 ml) and added dropwise to a mixture of concentrated NH$_4$OH (200 ml) and CH$_2$Cl$_2$ (120 ml). The mixture was vigorously stirred at room temperature for 24 hours. Water (200 ml) was added, the phases were separated and the aqueous layer was extracted with ethyl acetate (3×200 ml). The combined organic layers were dried (MgSO$_4$) and concentrated. Crystallization from CH$_2$Cl$_2$ gave 16.00 g (85%) of 12 as colorless crystals, mp 153°–154° C. IR (KBr): 3400 (N—H), 3180 (N—H), 1510 (C=C) cm$^{-1}$. $^1$H NMR δ8.11 (d, 1 arom H), 7.85 (d, 1 arom H), 7.78 (d, 1 arom H), 7.54–7.26 (8 arom H), 6.18 (s, 1 NH), 6.09 (s, 1 NH), 5.26 (s, 1 CH$_2$). Anal. (C$_{18}$H$_{15}$NO$_2$) C, H, N.

EXAMPLE 10

Ethyl 2-(Benzyloxy)-1-naphthimidate (13)

Triethyloxonium hexafluorophosphate (19.20 g, 58,1 mmol) was added to a solution of 12 (16.00 g, 57.7 mmol) in CH$_2$Cl$_2$ (710 ml). The solution was stirred at room temperature for 24 hours and then poured into ice-cold 0.5M K$_2$CO$_3$ (700 ml). The phases were separated and the aqueous layer was extracted with CH$_2$Cl$_2$ (2×100 ml). The organic layers were dried and concentrated. Chromatography with CH$_2$Cl$_2$ as the eluant gave 15.21 g (86%) of 13 as colorless crystals, mp 55°–56° C. IR (KBr): 3325 (N—H), 2975 (C—H), 1640 (C=C) cm$^{-1}$. $^1$H NMR: δ7.80–7.72 (3 arom H), 7.50–7.21 (8 arom H), 6.77 (s, 1 NH), 5.20 (s, 1 CH$_2$), 4.48 (q, 1 CH$_2$, J=7 Hz), 1.40 (t, 1 CH$_3$). Anal. (C$_{20}$H$_{19}$NO$_2$) C, H, N.

EXAMPLE 11

Ethyl 2-Hydroxy-1-naphthimidate (14)

Palladium on carbon (10%, 2.57 g) was introduced into a solution of 13 (15.21 g, 49.8 mmol) in ethanol (430 ml). The suspension was stirred under a hydrogen atmosphere for 6 hours. After filtration through Celite, the filtrate was concentrated, giving 10.11 g (94%) of 14 as yellow crystals, mp 145°–146° C. IR (KBr): 2980 (C—H), 1620 (C=C), 1085 (C—O) cm$^{-1}$. $^1$H NMR: δ8.65 (d, 1 arom H), 7.76 (d, 1 arom H), 7.71 (d, 1 arom H), 7.47 (m, 1 arom H), 7.29 (m, 1 arom H), 7.15 (d, 1 arom H), 4.29 (q, 1 CH$_2$, J=7 Hz), 1.42 (t, 1 CH$_3$). Anal. (C$_{13}$H$_{13}$NO$_2$) C, H, N.

EXAMPLE 12

3-Acetoxy-2-naphthoic Acid (16)

Concentrated sulfuric acid (8 drops) was added to a refluxing mixture of 15 (40.00 g, 213 mmol) in acetic anhydride (38 ml, 426 mmol). The mixture was maintained at reflux for 5 minutes. After cooling to room temperature, the solid was filtered off, washed with acetic acid and ethanol and dried under high vacuum to yield 40.31 g (82%) of 16 as pale yellow crystals, mp 185°–186° C. (lit. mp 184°–186° C.).

EXAMPLE 13

3-Hydroxy-2-naphthamide (18)

Oxalyl chloride (65 ml, 350 mmol) was added dropwise to a solution of 16 (40.31 g, 175 mmol) in DMF (17.2 ml) and dry toluene (850 ml). The mixture was stirred at room temperature for 1 hour. The toluene layer was separated from DMF and concentrated. The residue was taken up in toluene (500 ml) and concentrated again, providing 42.02 g (97%) of 17 as yellow crystals, which were dissolved in CH$_2$Cl$_2$ (500 ml) and added dropwise to a mixture of concentrated NH$_4$OH (420 ml) and CH$_2$Cl$_2$ (250 ml). The mixture was vigorously stirred at room temperature for 24 hours and then acidified to a pH of 3 with 9% HCl (1.60 L). Precipitate was filtered off, washed with water (4×150 ml) and dried under high vacuum, providing 29.95 g (95%) of 18 as yellow crystals, mp 216°–217° C. (lit. mp 217°–218° C.).

EXAMPLE 14

3-Acetoxy-2-naphthamide (19)

Acetic anhydride (19.2 ml, 200 mmol) was added to a solution of 18 (29.95 g, 160 mmol) in pyridine (32 ml, 400 mmol) and the mixture was maintained at room temperature for 30 minutes. The solid was filtered off, washed with acetone and dried (MgSO$_4$), generating 27.06 g (74%) of 19 as pale yellow crystals, mp 201°–202° C. (lit. 203°–205° C.).

EXAMPLE 15

3-Hydroxy-2-naphthonitrile (20)

A mixture of 19 (4.96 g, 21.6 mmol) and thionyl chloride (6.32 ml, 86.4 mmol) was heated under reflux for 2 hours. The solution was concentrated in vacuo to dryness. The residue was taken up in water (10 ml), methanol (200 ml) and 1N NaOH solution (75 ml). The solution was stirred at room temperature for 19 hours and concentrated. Chromatography, eluting with 1:1 cyclohexane/ethyl acetate, provided 2.41 g (66%) of 20 as yellow crystals, mp 188°–189° C. (lit. mp 188°–189° C.).

I claim:

1. A compound of the formula:

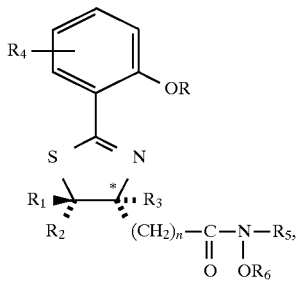 (I)

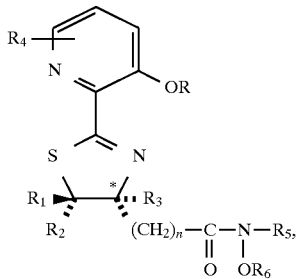 (II)

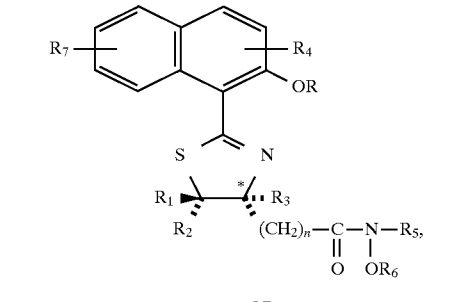 (III)

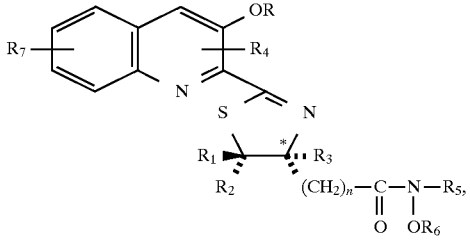 (IV)

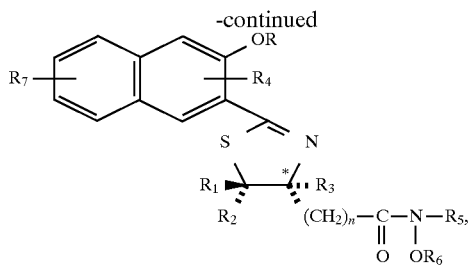 (V)

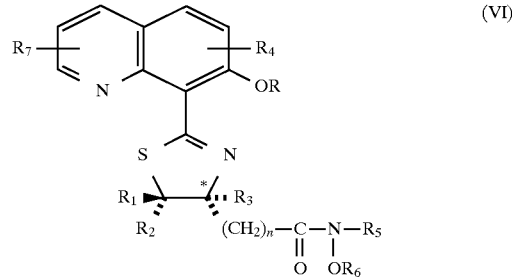 (VI)

wherein:

R may be H or acyl;

$R_1$, $R_2$, $R_3$, $R_4$ and $R_7$ may be the same or different and represent H, alkyl or hydrocarbyl arylalkyl having up to 14 carbon atoms, or

wherein x is 1–10 and y is 0–10;

$R_5$ is H, alkyl having up to 15 carbon atoms,

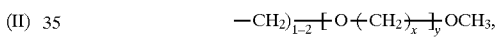

wherein x is 1–10 and y is 0–10, or

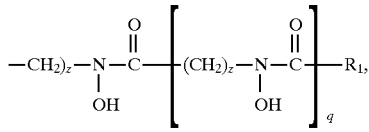

wherein $R_1$ is as defined above, z is 1–10 and q is 0–5;

$R_6$ is H or acyl;

n is 0–10;

a salt thereof with a pharmaceutically acceptable acid, or a pharmaceutically acceptable complex thereof.

2. A compound according to claim 1 having the formula I wherein $R=R_1=R_2=R_3=R_4=R_6=H$; $R_5$ is methyl and n=0.

3. A compound according to claim 1 having the formula I wherein $R=R_1=R_2=R_3=R_4=R_5=R_6=H$ and n=0.

4. A compound according to claim 1 having the formula III wherein $R=R_1=R_2=R_3=R_4=R_6=H$; $R_5$ is methyl and n=0.

5. A compound according to claim 1 having the formula III wherein $R=R_1=R_2=R_3=R_4=R_5=R_6=H$ and n=0.

6. A compound according to claim 1 having the formula V wherein $R=R_1=R_2=R_3=R_4=R_6=H$; $R_5$ is methyl and n=0.

7. A compound according to claim 1 having the formula V wherein $R=R_1=R_2=R_3=R_4=R_5=R_6=H$ and n=0.

8. An optically pure compound according to claim 1.

9. A pharmaceutical composition in unit dosage form comprising a therapeutically effective amount of a compound according to claim 1 and a pharmaceutically acceptable carrier therefor.

10. A method of preventing or treating a pathological condition in a human or non-human animal that is associated with an excess of a trivalent metal, ion or compound thereof comprising administering to said animal a therapeutically effective amount of a compound according to claim 1.

* * * * *

UNITED STATES PATENT AND TRADEMARK OFFICE
CERTIFICATE OF CORRECTION

PATENT NO. : 5,840,739
DATED : November 24, 1998
INVENTOR(S) : Raymond J. BERGERON, JR.

It is certified that error appears in the above-identified patent and that said Letters Patent is hereby corrected as shown below:

On the title page, delete the paragraph under "Related U.S. Application Data" in its entirety and substitute therefor the following:

-- Continuation-in-part of Ser. No. 532,805, Nov. 9, 1995 (abandoned), which claims priority based on International Application No. PCT/US 93/10936, Nov. 12, 1993, which claims priority based on Ser. No. 976,635, Nov. 16, 1992 (abandoned) --

In column 1, delete the first paragraph in its entirety and substitute therefor the following:

-- This application is a continuation-in-part of Ser. No. 08/532,805, Nov. 9, 1995 (abandoned), which claims priority based on International Application No. PCT/US 93/10936, Nov. 12, 1993, which claims priority based on Ser. No. 07/976,635, Nov. 16, 1992 (abandoned). --

Signed and Sealed this

Twenty-sixth Day of October, 1999

Attest:

Q. TODD DICKINSON

*Attesting Officer*     *Acting Commissioner of Patents and Trademarks*